Figure 1:
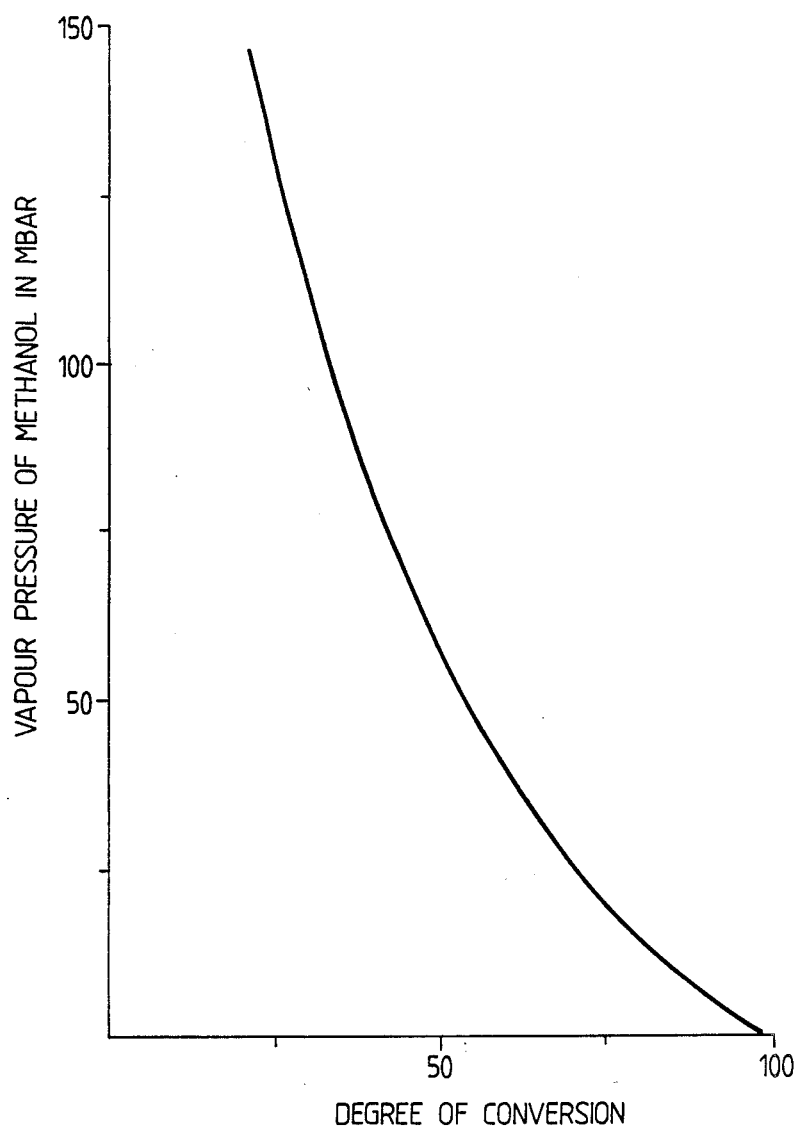

United States Patent [19]

Willemse

[11] Patent Number: 4,973,682

[45] Date of Patent: Nov. 27, 1990

[54] PROCESS FOR THE SYNTHESIS OF POLYOL FATTY ACID POLYESTERS

[75] Inventor: Gerardus W. M. Willemse, Vlaardingen, Netherlands

[73] Assignee: Lever Brothers Company, New York, N.Y.

[21] Appl. No.: 290,966

[22] Filed: Dec. 28, 1988

[30] Foreign Application Priority Data

Dec. 29, 1987 [GB] United Kingdom ................. 8730266

[51] Int. Cl.$^5$ .................... C07H 13/02; C07H 11/00; C07H 15/04; C07G 17/00
[52] U.S. Cl. .................................. 536/119; 536/115; 536/124; 536/120; 536/127
[58] Field of Search ................. 536/119, 115, 124, 120

[56] References Cited

U.S. PATENT DOCUMENTS

| | | | |
|---|---|---|---|
| 3,963,699 | 6/1976 | Rizzi et al. | 260/410.6 |
| 4,517,360 | 5/1985 | Volpenhein | 536/119 |
| 4,518,772 | 5/1985 | Volpenhein | 536/119 |

FOREIGN PATENT DOCUMENTS

| | | | |
|---|---|---|---|
| 0132293 | 1/1985 | European Pat. Off. | 536/119 |
| 0227137 | 9/1985 | Fed. Rep. of Germany | 536/119 |

*Primary Examiner*—Ronald W. Griffin
*Assistant Examiner*—Everett White
*Attorney, Agent, or Firm*—Gerard J. McGowan, Jr.

[57] ABSTRACT

The invention pertains to a process for the synthesis of polyol fatty acid polyesters comprising a two-stage transesterification of polyol to polyester, involving a pressure control such that in the first stage the esterification is not allowed to proceed beyond the mono- and/or oligoester, and in the second stage the esterification is continued to the polyester product.

15 Claims, 1 Drawing Sheet

PROCESS FOR THE SYNTHESIS OF POLYOL FATTY ACID POLYESTERS

The present invention relates to a process for the synthesis of polyol fatty acid polyesters wherein a substantially solvent-free complete reaction mixture of a polyol, optionally in admixture with fatty acid oligoesters thereof, a fatty acid lower-alkylester, a transesterification catalyst, and optionally an emulsifier, is caused to react under transesterification conditions of elevated temperature and reduced pressure. The invention particularly, but not exclusively, relates to a process for the synthesis of sugar fatty acid polyesters.

By "polyol" is meant any aliphatic or aromatic compound which comprises at least four free hydroxyl groups. In particular such polyols include the group of sugar polyols, which comprise the sugars, i.e. the mono-, di- and polysaccharides, the corresponding sugar alcohols and the derivatives thereof having at least four free hydroxyl groups. Examples of sugar polyols include glucose, mannose, galactose, xylose, fructose, sorbose, tagatose, ribulose, xylulose, lactose, maltose, raffinose, cellobiose, sucrose, erythritol, mannitol, lactitol, sorbitol, xylitol and α-methylglucoside. A generally used sugar polyol is sucrose.

The term "polyol fatty acid ester" is intended to include any such polyesters or mixtures thereof having a degree of conversion of at least 70%. The degree of conversion is defined as the percentage of polyol hydroxyl groups of the polyol fatty acid polyester that on an average have been esterified with fatty acids, a degree of conversion of 100% corresponding to the fully esterified polyol.

In this specification by "fatty acid" is meant $C_8$–$C_{24}$ fatty acids which may be saturated or unsaturated, and may have straight or branched alkyl chains.

The polyol fatty acid polyesters are known to be suitable low-calorie fat-replacers in edible products. Substantially indigestible by human beings they have physical and organoleptic properties very similar to triglyceride oils and fats conventionally used in edible products. Polyol fatty acid polyesters are further reported to have use as pharmaceutical agents in view of their ability to take up fat-soluble substances, such as in particular cholesterol, in the gastro-intestinal tract, and subsequently remove these substances from the human body.

In general polyol fatty acid polyesters are synthesized by a process in which a polyol, such as a mono- or disaccharide, is reacted with a fatty acid lower-alkylester, often the fatty acid methylester, in the presence of a transesterification catalyst, such as e.g. an alkali metal hydroxide or carbonate. In a first stage a polyol fatty acid mono- or oligoester is formed, which in a second stage after subsequent addition of further fatty acid lower-alkylester is reacted to form polyesters of the desired degree of conversion. Under certain conditions the two stages of the reaction can be combined into a single reaction.

Processes of this type are described in e.g. the U.S. Pat. Nos. 3,963,699, 4,517,360, and 4,518,772.

Particularly with single step esterification processes, i.e. where all fatty acid lower-alkylester is added simultaneously, one of the problems is that it proves difficult to have all the polyol starting material participate in the reaction. Unless special measures are taken to control the transesterification at an early stage of the reaction, a considerable portion of the polyol (which may be as high as 80% by weight or more dependent on the molar ratio between polyol and catalyst) is excluded from the transesterification reaction and remains unreacted. This results in poor yields of polyester and caramelization of the unreacted polyol during the course of the reaction.

A further problem is excessive foam formation during in particular the initial stage of the reaction which renders the reaction system difficult to control on a technical scale.

It has now been found that the above problems are substantially overcome when the partial vapour pressure of the lower-alkyl alcohol which is formed from the fatty acid lower-alkylester during the transesterification reaction, is controlled such that in an initial stage the transesterification reaction cannot proceed beyond a degree of conversion which corresponds to esterification to the polyol monoester and/or oligoesters. Using such a pressure control, substantially all polyol will participate in the subsequent continued transesterification reaction, thereby resulting in a high yield process. Such pressure control also eliminates or substantially reduces the problem of excessive foam formation, particularly pertinent during the initial stages of the reaction.

Accordingly, the present invention provides a process for the synthesis of polyol fatty acid polyesters wherein a substantially solvent-free complete reaction mixture of a polyol, optionally in admixture with fatty acid oligoesters thereof, a fatty acid lower-alkylester, a transesterification catalyst, and optionally an emulsifier, is caused to react under transesterification conditions of elevated temperature and reduced pressure, said pressure being controlled such that in an initial stage (1) said polyol is esterified to a degree of conversion within the range of 10 to 50% substantially without leaving non-participating polyol, and in a subsequent final stage (2) the reaction is caused to proceed to a degree of conversion of at least 70%.

By "complete reaction mixture" is meant that in such a mixture all reactants are present in the amounts necessary to achieve the desired final reaction product without further additions of such reactants during the course of the reaction.

By "non-participating polyol" is meant any polyol material that will remain unreacted throughout the transesterification reaction. It does not include polyol material that, although not yet esterified, is present in dissolved or microemulsified form, which with increasing degree of conversion will yet be esterified. By "substantially without leaving non-participating polyol" is meant that less than 10% by weight of the initial polyol has remained or will remain unreacted.

An essential element of the process of the present invention is that the pressure above the reaction mixture during the first part of the esterification reaction is controlled such that on the one hand the esterification is not allowed to proceed beyond the stage of conversion to mono- or oligoester, and on the other hand all polyol is involved in the reaction before the reaction is continued to high or full esterification.

This is suitably achieved when particularly during the final part of an initial stage (1) of the reaction the pressure above the reaction mixture is controlled to a level of within 30 mbar, and preferably within 15 mbar from the equilibrium vapour pressure of the lower alkyl alcohol which corresponds to a degree of conversion within the range of from 10 to 30%. Control of the pressure above the reaction mixture results in control of the partial vapour pressure of the lower-alkyl alcohol and thereby in control of the concentration of the alcohol in the reaction mixture.

Correspondingly, the degree of conversion after the initial stage (1) lies within the range of from 10 to 50%, and preferably within the range of from 10 to 30%.

The equilibrium vapour pressure of the lower alkyl alcohol is a function of the temperature and the degree of conversion, and can easily be determined by conventional techniques. In FIG. 1 a plot is shown illustrating the relationship between the equilibrium vapour pressure above the reaction mixture and the degree of conversion at 125° C. for a reaction of sucrose and fatty acid (soybean) methylester.

Under the preferred transesterification conditions to be described hereunder in more detail the pressure above the reaction mixture is suitably controlled to a level within the range of from 60 to 180 mbar, and preferably of from 90 to 150 mbar during the final part of the initial stage (1).

During a first part of stage (1) the esterification reaction has to be initiated. During this first part it is of advantage to apply a reduced pressure as low as possible or economically feasible. At this stage pressures of below e.g. 25 mbar, or even below 10 mbar are suitable.

Before continuing the esterification after the initial stage (1) substantially no non-participating polyol should be present in the reaction mixture. In particular, after initial stage (1) non-participating polyol levels should be less than 10% by weight of the starting amount, and preferably is less than 5%, or even less than 1% by weight of the starting amount of polyol.

Subsequent to the initial stage (1), i.e. once the polyol is esterified to a degree of conversion within the range of 10 to 50% and substantially no non-participating polyol is present any more, the pressure can be suitably further reduced to a level of less than 25 mbar during the final stage (2). Preferably, during the final stage (2) even lower pressures are applied, in particular of less than 10 mbar, and most preferably less than 5 mbar. During this stage the polyol fatty acid oligoester-containing reaction mixture resulting after the initial stage (1), is further reacted to the desired polyol fatty acid polyester product. Preferably, the esterification is continued to a degree of conversion of at least 90%, and most preferably to a degree of esterification of at least 95%.

Both stages of the transesterification reaction can suitably be carried out at a similar temperature which normally lies within the range of from 100° to 180° C. It has been found of advantage to raise slightly the temperature during stage (2) of the reaction. Preferably temperatures are applied within the range of from 110° to 160° C., the range of from 120° to 150° C. being preferred most.

It is preferred to apply agitation to the reaction mixture, in particular throughout the initial stage of the reaction e.g. by way of stirring means in the reaction vessel.

In view of the difference in pressure regime during the initial and final stage of the reaction it may be of advantage to use a reaction system comprising two separate reaction vessels each equipped with pressure control means optimised to the specific reduced pressure regime needed. In this way very expensive pressure control means capable of coping with a wide range of pressures and quantities of lower-alkyl alcohol to be removed can be avoided.

Suitably, the lower-alkyl alcohol formed during the esterification reaction from the lower-alkylester is condensed in suitable condensor means after removal thereof from the reaction mixture, and collected for subsequent use or re-use.

In general the reactants used in the transesterification reaction in accordance with the process of the present invention comprise a polyol, optionally in admixture with a fatty acid oligoester thereof, a fatty acid lower alkylester, a transesterification catalyst, and, optionally an emulsifier. In the preparation of the mixture of reactants also solvents, such as water and/or lower-alkyl alcohols, may optionally be introduced separately from or together with one or more of these reactants.

The polyol can be any of those as defined hereinbefore, or a mixture thereof. Preferred polyol starting materials are the sugar polyols, and in particular sucrose. The polyol starting material does not necessarily consist solely of non-esterified polyols. It may in addition comprise polyol oligoesters of fatty acids, such as mono-, di- and/or triesters, which are intermediates in the conversion of polyols to the polyol fatty acid polyesters.

Suitable fatty acid lower-alkylesters are fatty acid esters of the group of lower alcohols including mono-, di- and triols. In particular, the ester is derived from the $C_1$–$C_5$ mono-alcohols, preferably methanol. The fatty acid residues can be any of those as defined hereinbefore, the selection of which is dependent on the specific polyol fatty acid esters desired.

The amount of fatty acid lower-alkylester is dependent on the desired degree of conversion. In the synthesis of polyol polyesters having high degrees of conversion in general excess amounts of fatty acid lower-alkylester are used. More particularly, when fully converted sucrose polyesters are aimed at, good results are obtained when a molar ratio of fatty acid lower-alkylester: sucrose is used within the range of from 10:1 to 20:1, in particular, of from 10:1 to 15:1, or even 10:1 to 14:1.

Suitable transesterification catalysts include the group consisting of alkali metals, alkaline earth metals, and alloys thereof, as well as the alkoxides, bicarbonates, carbonates, hydrides, and hydroxides of such metals. KOH has been found to be particularly suitable, but also NaOH and the corresponding carbonates, and bicarbonates of potassium or sodium can be advantageously used. Although one might argue that the above reagents are not the catalysts themselves, but are reagents forming the catalyst, in this specification as is done in the literature relating to similar processes, this group will be referred to as catalysts.

The catalyst is used in an amount corresponding to a molar ratio of catalyst: polyol of at least 0.01:1, and preferably of 0.05:1 to 1:1.

In general it is attractive to use an emulsifier to improve contact among the polyol, the catalyst and the fatty acid lower-alkylester particularly during the initial stages of the esterification reaction. Many types of alkali-resistant emulsifiers can suitably be used, such as edible emulsifiers including phosphatides, such as lecithin, mono- and diglycerides and sugar oligoesters of fatty acids, in particular the mono-and diesters, and detergents, such as soaps and alkali metal alkyl sulphates.

Preferred emulsifiers are alkali metal soaps derived from any of the fatty acids as defined hereinbefore. It has been found that conversion rates of polyol to polyol fatty acid ester are improved when fatty acid soap emulsifiers are used comprising at least 15%, but preferably even at least 75% of short chain fatty acid soap. Such short chain fatty acid soap is characterized by a fatty acid chain length of less than 15 carbon atoms, and in particular within the range of 6 to 12 carbon atoms, such as coconut soap.

Particularly, when the emulsifier is selected from the group of alkali metal soaps, it may be convenient to introduce the emulsifier into the reaction mixture in the form of a precursor thereof, such as the corresponding free fatty acids. In such a case the composition of the reactant mixture should be such that the precursor is converted to the corresponding emulsifier after addition to and mixing with the reactant mixture.

When free fatty acids are used as emulsifier precursors, an alkaline material should be present in the reaction mixture suitable to convert the fatty acid precursor into the corresponding soap emulsifier. Suitably, the transesterification catalyst can be used to effectuate such a conversion. Accordingly, the amount of catalyst should be sufficient to ensure both proper catalytic action during the esterification, as discussed hereinbefore, and full neutralization of such a soap precursor to the corresponding soap.

Suitable amounts of emulsifier lie within the range of from 0.1 to 15% by weight, preferably of from 0.1 to 12%, and most preferably of from 0.2 to 6% by weight of the total reactant mixture.

Optionally, one or more solvents may be introduced separately from or together with the various reactants to improve addition and mixing thereof. Suitable solvents include water and/or lower alcohols, such as $C_1$–$C_5$ alcohols, in particular methanol. The solvent is subsequently removed before or at the start of the transesterification reaction.

Advantageously, the reaction mixture is spray-dried before starting the esterification reaction to achieve a homogenized and substantially solvent-free reaction mixture particularly suitable as starting mixture for the subsequent esterification in accordance with the present invention.

In this specification the term "homogenized" means intimately mixed and is not restricted to homogenized in a narrow microscopic sense.

By "substantially solvent-free" is meant comprising less than 0.5% of solvent. Solvent levels at the start of the esterification reaction of less than 0.1, or even 0.05% are preferred.

Spray-drying is suitably effected by passing the initial mixture of reactants through a spraying nozzle into a drying chamber. Intimate mixing occurs due to the dissipation of energy on passing through the spraying nozzle. Evaporation of the solvent occurs in the drying chamber, the resulting vapour continuously being removed from the drying chamber by suitable reduced pressure or gas flow conditions. Adequate solvent evaporation may be established by a variety of per se conventional techniques, including the application of reduced pressure and/or elevated temperature conditions, or the use of, optionally heated, co-current, counter-current or mixed-current inert gas flows.

In a batch-wise operation the drying chamber is also suitably used as reaction vessel for the transesterification reaction. In a continuous or semi-continuous operation the drying chamber and reaction vessel preferably are separate.

It may be of further advantage to pre-mix the reactants before passing through the spraying nozzle by an alternative agitation step for example employing a dynamic or static mixer, or flow restriction in the feed line to the spraying nozzle.

It is preferred to prepare the reactant mixture by way of the following process.

In an initial step the polyol or the fatty acid oligoester thereof is mixed with the catalyst in a liquid system so as to form the corresponding polyol anion. The formation of the actual polyol anion may be immediate or only be realized under substantially solvent-free conditions. Preferably, the contact between the polyol or the oligoester thereof and the catalyst are mixed in the presence of a solvent, which is subsequently removed in the spray-drying step in accordance with the present invention. Most preferably, the polyol or the oligoester thereof and the catalyst are first partially or fully dissolved in a solvent and subsequently mixed. Suitable such solvents include water, lower alcohols and mixtures thereof. In particular water is a suitable solvent if potassium or sodium hydroxide is used as the transesterification catalyst.

In a subsequent step the fatty acid lower-alkylester, optionally in combination with the emulsifier, is added to the liquid system. After addition of the fatty acid lower-alkylester the reaction mixture is conveniently spray-dried.

As stated hereinbefore alkali metal soaps or suitable precursors thereof such as the corresponding free fatty acids are preferred emulsifiers particularly to assist in the start-up and initial stages of the esterification reaction. Although very suitable in terms of the esterification reaction a drawback that may be attached to the use of soaps is the fact that the spray-drying thereof necessitates relatively frequent cleaning of the spray-drying equipment. In particular on a technical scale this is undesirable.

Accordingly, it is preferred to add the emulsifier component, particularly soap emulsifiers or precursors thereof, to the reaction mixture only after the spray-drying step. Using this route the relatively frequent cleaning of the spray-drying equipment can be avoided.

The degree to which desolvatization is achieved in the spray-drying step, is the resultant of economic and process-technical factors, such as in particular the amount of solvent to be removed and the corresponding energy input or temperature required in the drying chamber.

Accordingly, instead of using spray-drying conditions resulting in full removal of solvent, it may be of advantage to have the spray-drying step followed by a further 'post-drying' treatment which drives the removal of residual solvent to substantial completion. Any such conditions resulting in evaporation of any residual solvent still present after spray-drying or introduced in the post spray-drying addition of the emulsifier component, may be suitable and include temperature and reduced pressure conditions, stripping with suitable stripping agents, such as preferably methanol, or inert gases, such as nitrogen, or submitting the reaction mixture to a further spray-drying step.

Preferably, the reaction mixture is submitted to conditions of elevated temperature and reduced pressure suitable for drying. Drying temperatures lie below about 110° C., and preferably within the range of 60° to 100° C. Suitably, these post-drying conditions are maintained for periods of up to several hours, periods of 0.5 to 3 hours being preferred.

Suitably the solvent level of the reaction mixture is reduced to below 0.5% in the spray-drying step and further reduced to below 0.1% in the subsequent post-drying step. Preferably, the solvent level is reduced to below 0.1% in the spray-drying step and to below 0.05% in the post-drying step.

If so desired a supplementary amount of polyol may be introduced to the starting mixture of reactants before starting the transesterification reaction.

EXAMPLE 1

A mix of 89% by weight of soybean-derived fatty acid methylesters and 3% by weight of potassium coconut soap was prepared by spray-drying. A further 6% by weight of sucrose powder was dispersed into this mixture. Subsequently, the mixture of reactants was heated to 125° C. and the pressure in the reaction vessel was reduced to 3 mbar. At the first formation of vapour bubbles of methanol the reaction vessel was closed and the pressure inside the vessel was allowed to increase to about 120 mbar due to the formation of methanol. This pressure was maintained and controlled by means of an automatic regulating valve. After 2 hours of reaction time a homogeneous mixture had been formed, the degree of conversion being about 20%. Then the pressure was decreased to 3 mbar accompanied by vigorous boiling and fast removal of the methanol from the reaction mixture. After 6 hours of reaction time the degree of conversion had reached approximately 70% and no unreacted sucrose was left.

For reasons of comparison the same process was repeated but without allowing the pressure to increase to 120 mbar at the first formation of methanol bubbles. Instead the pressure was maintained at 3 mbar during the full reaction time. After 6 hours of reaction time the degree of conversion had reached a level of only 20%, the final reaction mixture still containing about 5.5% by weight of unreacted sucrose.

EXAMPLE 2

An intimate mix of 89.5 parts by weight of fatty acid (soybean) methylester, 3.0 parts by weight of potassium soap (coconut) and 2.0 parts by weight of potassium sucrate was prepared by spray-drying. A further 5.5 parts by weight of sucrose was dispersed into this mixture.

Subsequently, the mixture of reactants was heated to 125°–135° C., and the pressure reduced to a level of about 5 mbar. After about 15 minutes the sucrose started to react under formation and evaporation of methanol causing slight foaming. At this point of time the pressure was allowed to gradually (in about 15 minutes) increase to about 100 mbar. The pressure was maintained at this level for about 3 hours, after which period the reaction mixture was homogeneous (no unreacted sucrose) and the degree of conversion had reached a value of about 18% as calculated from the amount of methanol formed and collected during this period.

Subsequently the pressure was again reduced to a level of about 1 mbar, and the temperature slightly raised to about 150° C. After about 4 hours the reaction yielded sucrose polyester having a degree of conversion of about 90%.

I claim:

1. A process for the synthesis of polyol fatty acid polyesters wherein a complete reaction mixture, having less than 0.5% of solvent, of a polyol, a fatty acid lower-alkylester, and a transesterification catalyst, is caused to react under transesterification conditions of elevated temperature and reduced pressure, said pressure being controlled such that
   in an initial stage (1) said polyol is esterified to a degree of conversion within the range of 10 to 50% such that less than 10% by weight of the initial polyol remains as non-participating polyol, and
   in a subsequent final stage (2) the reaction is caused to proceed to a degree of conversion of at least 70%.

2. Process according to claim 1 wherein during the final part of said initial stage (1) the pressure is controlled to a level of within 30 mbar from the equilibrium vapour pressure of the lower alkyl alcohol corresponding to a degree of conversion within the range of from 10 to 30%.

3. Process according to claim 2 wherein during said final part of initial stage (1) the pressure is controlled to a level of within 15 mbar from the equilibrium vapour pressure of the lower alkyl alcohol corresponding to a degree of conversion within the range of from 10 to 30%.

4. Process according to claim 1 wherein during the final part of said initial stage (1) the pressure is controlled to a level within the range of from 60 to 180 mbar.

5. Process according to claim 4 wherein during said final part of initial stage (1) the pressure is controlled to a level within the range of from 90 to 150 mbar.

6. Process according to claim 1 wherein during the first part of said initial stage (1) the pressure is controlled to a level of below 25 mbar.

7. Process according to claim 1 wherein during said final stage (2) the pressure is reduced to a level of below 25 mbar.

8. Process according to claim 7 wherein during said final stage (2) the pressure is reduced to a level of below 5 mbar.

9. Process according to claim 1 wherein the transesterification reaction is carried out at a temperature within the range of from 110° to 160° C.

10. Process according to claim 1 wherein in said initial stage (1) the polyol is esterified to a degree of conversion within the range of from 10 to 30%.

11. Process according to claim 1 wherein in said final stage (2) the transesterification is continued to a degree of conversion of at least 90%.

12. Process according to claim 1 used for the synthesis of sucrose fatty acid polyesters.

13. The process according to claim 1 wherein said complete reaction mixture further comprises an emulsifier.

14. The process according to claim 1 wherein said complete reaction mixture further comprises fatty acid oligoesters of said fatty acid polyesters.

15. The process according to claim 1 wherein said complete reaction mixture includes less than 0.1% solvent.

* * * * *